US009128088B2

(12) United States Patent
Riccardi et al.

(10) Patent No.: US 9,128,088 B2
(45) Date of Patent: Sep. 8, 2015

(54) EFFECTIVE NEW DRUG TARGET FOR THE TREATMENT OF TUBERCULOSIS

(75) Inventors: Giovanna Riccardi, Pavia (IT); Giulia Manina, Pavia (IT); Maria Rosalia Pasca, Pavia (IT)

(73) Assignee: UNIVERSITA' DEGLI STUDI DI PAVIA (IT)

( * ) Notice: Subject to any disclaimer, the term of this patent is extended or adjusted under 35 U.S.C. 154(b) by 972 days.

(21) Appl. No.: 12/867,049

(22) PCT Filed: Feb. 13, 2008

(86) PCT No.: PCT/EP2008/001088
§ 371 (c)(1),
(2), (4) Date: Nov. 18, 2010

(87) PCT Pub. No.: WO2009/100731
PCT Pub. Date: Aug. 20, 2009

(65) Prior Publication Data
US 2011/0262361 A1    Oct. 27, 2011

(51) Int. Cl.
| A61K 39/04 | (2006.01) |
| A61K 49/00 | (2006.01) |
| A61K 48/00 | (2006.01) |
| G01N 33/569 | (2006.01) |

(52) U.S. Cl.
CPC ............ *G01N 33/5695* (2013.01); *A61K 39/04* (2013.01); *G01N 2333/35* (2013.01); *G01N 2500/04* (2013.01)

(58) Field of Classification Search
CPC ....... A61K 39/04; A61K 38/43; A61K 49/00; A01N 63/00; C12Q 1/02; C12Q 1/18; C12Q 1/34; C12R 1/01; C12R 1/64
USPC ........................ 424/9.1, 9.2, 93.1, 93.2, 248.1
See application file for complete search history.

(56) References Cited

U.S. PATENT DOCUMENTS

| 3,522,247 A | 7/1970 | Cronin et al. | |
| 2002/0151008 A1 | 10/2002 | Alland | 435/183 |
| 2003/0013090 A1 | 1/2003 | Barry | 435/6 |
| 2006/0052371 A1 * | 3/2006 | Kajino et al. | 514/224.2 |

FOREIGN PATENT DOCUMENTS

| WO | 01/35317 | 5/2001 |
| WO | 2005/092872 | 10/2005 |
| WO | 2007/134625 | 11/2007 |

OTHER PUBLICATIONS

International Search Report for PCT/EP2008/001088 filed on Feb. 13, 2008 in the name of Universita' Degli Studi Di Pavia.
Written Opinion for PCT/EP2008/001088 filed on Feb. 13, 2008 in the name of Universita' Degli Studi Di Pavia.
Seidel, M. et al. Identification of a novel arabinofuranosyltransferase AftB involved in a terminal step of cell wall arabinan biosynthesis in corynebacterianeae, such as *Corynebacterium glutamicum* and *Mycobacterium tuberculosis*. Journal of Biological Chemistry, vol. 282, No. 20, pp. 14729-14740 (May 2007).
Alderwick, L.J. et al. Identification of a novel arabinofuranosyltransferase (AftA) involved in cell wall Arabinan biosynthesis in *Mycobacterium tuberculosis*. Journal of Biological Chemistry, vol. 281, No. 23, pp. 15653-15661 (Jun. 2006).
Wolucka, B.A. et al. Biosynthesis of D-arabinose in mycobacteria—a novel bacterial pathway with implications for antimycobacterial therapy. The FEBS Journal, vol. 275, No. 11, pp. 2691-2711 (Jun. 2008).
Shah, N.S. et al. Worldwide Emergence of Extensively Drug-resistant Tuberculosis. Emerg. Infect. Dis. vol. 13, No. 3, pp. 380-387 (2007).
Williams, K.J. et al. Current Strategies for Identifying and Validating Targets for New Treatment-Shortening Drugs for TB. Current Molecular Medicine, vol. 7, pp. 297-307 (2007).
Mikusova, K. et al. Decaprenylphosphoryl Arabinofuranose, the Donor of the D-Arabinofuranosyl Residues of Mycobacterial Arabinan, Is Formed via a Two-Step Epimerization of Decaprenylphosphoryl Ribose. Journal of Bacteriology, vol. 187, No. 23, pp. 8020-8025 (Dec. 2005).
Sassetti, C.M. et al. Genetic requirements for mycobacterial survival during infection. PNAS, vol. 100, No. 22, pp. 12989-12994 (Oct. 28, 2003).
Mullis, K. et al. Specific Enzymatic Amplification of DNA In Vitro: The Polymerase Chain Reaction. Cold Spring Harbor Symposium Quant. Biol. vol. 51, pp. 263-273 (1986).
Kohler, G. et al. Continuous cultures of fused cells secreting antibody of predefined specificity. Nature, vol. 256, pp. 495-497 (1975).
Anderson, A., et al., Recall of long-lived immunity to *Mycobacterium tuberculosis* infection in mice, The American Association of immunologists 1995, 154: 3359-3372.
Brennan, P., et al., The cell-wall core of *Mycobacterium tuberculosis* in the context of drug discovery, Current Topics in Medicinal Chemistry 2007, 7: 475-788.

(Continued)

*Primary Examiner* — Rodney P Swartz
(74) *Attorney, Agent, or Firm* — Steinfl & Bruno LLP

(57) ABSTRACT

The present invention allows a screening method for identifying novel drugs for the treatment of tuberculosis as well as a diagnostic method for identifying clinical strains that are resistant to these novel drugs. In particular, the present invention relates to a method for screening in vitro drug candidates for the treatment of tuberculosis by interfering with the arabinogalactan biosynthesis, the said method comprising a step of putting into contact a *Mycobacterium tuberculosis* cell culture over-expressing a protein that performs the transformation of decaprenyl-P-ribose to decaprenyl-P-arabinose and that can be encoded by rv3790 gene or homologues thereof or any open-reading artificial frame whose gene product is identical or homologue to Rv3790 protein, with a drug candidate and then evaluating the percentage of inhibition caused by the drug candidate against a control in an assay test, such as an antibacterial test or an enzymatic test.

22 Claims, 2 Drawing Sheets

(56) References Cited

OTHER PUBLICATIONS

TubercuList (retrieved on Apr. 18, 2012). Retrieved from the internet: http://www.ncbi.nlm.nih.gov/sutils/genomtable.cgi?organism=microb.

Cage, G.D., Direct Identification of *Mycobacterium* Species in BACTEC 7H12B Medium by High-Performance Liquid Chromatography, Journal of Clinical Microbiology, Feb. 1994, vol. 32, No. 2 pp. 521-524.

Pasca, M.R. et al., *mmpL7* Gene of *Mycobacterium tuberculosis* Is Responsible for Isoniazid Efflux in *Mycobacterium smegmatis*, Antimicrobial Agents and Chemotherapy, Nov. 2005, vol. 49, No. 11, pp. 4775-4777.

Genomic Blast (retrieved on Apr. 23, 2012) Retrieved from the internet: <URL:http://www.ncbi.nlm.nih.gov/sutils/genom_table.cgi?organism=microb>.

Network Protein Sequence Analysis (Retrieved on Apr. 23, 2012) Retrieved from the internet: <URL:http://www.npsa-pbil.ibcp.fr/cgi-bin/npsa_automat.pl?page=/NPSA/npsa_clustalw.html>.

Makarov, V., et al., 'Benzothiazinones Kill *Mycobacterium Tuberculosis* by Blocking Arabinan Synthesis' and Supplementary Materials. Science. 2009, 324: p. total: 26.

Pasca, M., et al., Clinical Isolates of *Mycobacterium Tuberculosis* in Four European Hospitals are Uniformly Susceptible to Benzothiazinones. Antimicrob. Agents and Chemo. 2010, p. 1616-1618.

Christophe, T., et al., High Content Screening Identifies Decaprenyl-Phosphoribose 2' Epimerase as a Target for Intracellular Antimycobacterial Inhibitors. *PLoS Pathogens*, 2009. 5(10): e1000645.

Magnet, S., et al., Leads for Antitubercular Compounds from Kinase Inhibitor Library Screens. Tuberculosis. 2010, p. 354-360.

Stanley, S., et al., Identification of Novel Inhibitors of *M. Tuberculosis* Growth Using Whole Cell Based High-Throughput Screening. *ACS Chem. Biol.* 2012, 7:1377-1384.

\* cited by examiner

Fig. 1. Multi-alignment analysis with Rv3790 orthologs

```
                                              361                                           401                                  421
                                              |                                             |                                    |
SEQ ID NO: 3   Rv3790 (Mycobacterium tuberculosis)      SFLNVFKLFGPRNQAPLSFPIPGWNIEVDFPIKDGLGKFVSELDRRVLEFGGRLYTAKDS
SEQ ID NO: 4   BCG_3852 (Mycobacterium bovis BCG)       SFLNVFKLFGPRNQAPLSFPIPGWNIEVDFPIKDGLGKFVSELDRRVLEFGGRLYTAKDS
SEQ ID NO: 5   Mb3819 (Mycobacterium bovis)             SFLNVFKLFGPRNQAPLSFPIPGWNIEVDFPIKDGLGKFVSELDRRVLEFGGRLYTAKDS
SEQ ID NO: 6   ML0109 (Mycobacterium leprae)            SFLNVFKLFGPGNQAPLSFPIPGWNIEVDFPIKSGLNEFVNKLDRRVMELGGRLYTAKDS
SEQ ID NO: 7   MAV_0232 (Mycobacterium avium)           SALNVFKLFGPGNRAPLSFPMAGWNVAMDFPNKPGVNEFLNELDRRVLQFGGRVVTAKDS
SEQ ID NO: 8   MAP0235c (M. avium paratuberculosis)     SALNVFKLFGPGNRAPLSFPMAGWNVAMDFPNKPGVNEFLNELDRRVLQFGGRVITAKDS
SEQ ID NO: 9   MSMEG_6382 (Mycobacterium smegmatis)     SFLNVFKLFGPGNQAPLSFPIPGWNVEVDFPIKAGLHEFVTELDRRVLEFGGRLYTAKDS
SEQ ID NO: 10  Mycobacterium aurum                      SFLNVFKLFGPRNQAPLSFPIPGWNISVDFPIKDGLGKFVSELDRRVLEFGGRLYTAKDS
SEQ ID NO: 11  Mycobacterium gilvum                     SPLNVFKLFGPGNQAPLSFPIPGWNVEVDFPITAGLNEFLNGLDKRVLEFGGRLYTAKDS
SEQ ID NO: 12  Mycobacterium vanbaleni                  SFLNVFKLFGAGNQAPLSFPIPGWNVEVDFQINPGLNEFLNGLDKRVLEFGGRLYTAKDS
SEQ ID NO: 13  Mycobacterium ulcerans                   SFLNVFKLFGEGNQAPLSFPIPGWNIEVDFPIKAGLNEFVSELDRRVRVMEFGGRLYTAKDS
SEQ ID NO: 14  Rhodococcus spp.                         SFLNVFKLFGPGNQAPLSFPIPGWNIEVDFRIKPGLNEFVTELDKRVLKFGGRLYTAKDS
SEQ ID NO: 15  Nocardia farcinica                       SFLNVFKYFGQGNQAPLSFPMPGWNVELDFPIKPGLNEFVTELDSRVLEFGGRLYTGKDS
SEQ ID NO: 16  Corynebacterium jeikeium                 SALNVFKLFGEGNKAPLSYPMPGWNVVDLPIKPGLGAFLDDLDRRVMEFGGRLYLAKES
SEQ ID NO: 17  Corynebacterium diphtheriae              SALNVFKLFGEGNKAPLSYPMPGWNVEVDFPIKPGLGAFLDDLDKRVMEFGGRLYLAKES
SEQ ID NO: 18  Corynebacterium efficiens                SALNVFKLFGPGNKAPLSYPMPGWNVEVDFPIRRGLGAFLDELLDERVMEFGGRLYLAKES
SEQ ID NO: 19  Corynebacterium glutamicum               SALNVFKLFGPGNRAPLSYPMPGWNVEVDFPIRPGLGAFLDDLDKRVMEFGGRLYLAKES
                                                        * ***** ** * *****:*:.***..:;*:       *: ** **::*****;* .*;*
```

Fig. 2 DNA sequence of Rv3790 gene (From genolist.pasteur.fr/TubercuList/).

SEQ ID NO: 2

```
   1 - atg ttg agc gtg gga gct acc act acc gcc
  31 - acc cgg ctg acc ggg tgg ggc cgc aca gcg
  61 - ccg tcg gtg gcg aat gtg ctt cgc acc cca
  91 - gat gcc gag atg atc gtc aag gcg gtg gct
 121 - cgg gtc gcc gag tcg ggg ggc ggc cgg ggt
 151 - gct atc gcg cgc ggg ctg ggc cgc tcc tat
 181 - ggg gac aac gcc caa aac ggc ggt ggg ttg
 211 - gtg atc gac atg acg ccg ctg aac act atc
 241 - cac tcc att gac gcc gac acc aag ctg gtc
 271 - gac atc gac gcc ggg gtc aac ctc gac caa
 301 - ctg atg aaa gcc gcc ctg ccg ttc ggg ctg
 331 - tgg gtc ccg gtg ctg ccg gga acc cgg cag
 361 - gtc acc gtc ggc ggg gcg atc gcc tgc gat
 391 - atc cac ggc aag aac cat cac agc gct ggc
 421 - agc ttc ggt aac cac gtg cgc agc atg gac
 451 - ctg ctg acc gcc gac ggc gag atc cgt cat
 481 - ctc act ccg acc ggc gag gac gcc gaa ctg
 511 - ttc tgg gcc acc gtc ggg ggc aac ggt ctc
 541 - acc ggc atc atc atg cgg gcc acc atc gag
 571 - atg acg ccc act tcg acg gcg tac ttc atc
 601 - gcc gac ggc gac gtc acc gcc agc ctc gac
 631 - gag acc atc gcc ctg cac agc gac ggc agc
 661 - gaa gcg cgc tac acc tat tcc agt gcc tgg
 691 - ttc gac gcg atc agc gct ccc ccg aag ctg
 721 - ggc cgc gcg gcg gta tcg cgt ggc cgc ctg
 751 - gcc acc gtc gag caa ttg cct gcg aaa ctg
 781 - cgg agc gaa cct ttg aaa ttc gat gcg cca
 811 - cag cta ctt acg ttg ccc gac gtg ttt ccc
 841 - aac ggg ctg gcc aac aaa tat acc ttc ggc
 871 - ccg atc ggc gaa ctg tgg tac cgc aaa tcc
 901 - ggc acc tat cgc ggc aag gtc cag aac ctc
 931 - acg cag ttc tac cat ccg ctg gac atg ttc
 961 - ggc gaa tgg aac cgc gcc tac ggc cca gcg
 991 - ggc ttc ctg caa tat cag ttc gtg atc ccc
1021 - aca gag gcg gtt gat gag ttc aag aag atc
1051 - atc ggc gtt att caa gcc tcg ggt cac tac
1081 - tcg ttt ctc aac gtg ttc aag ctg ttc ggc
1111 - ccc cgc aac cag gcg ccg ctc agc ttc ccc
1141 - atc ccg ggc tgg aac atc tgc gtc gac ttc
1171 - ccc atc aag gac ggg ctg ggg aag ttc gtc
1201 - agc gaa ctc gac cgc cgg gta ctg gaa ttc
1231 - ggc ggc cgg ctc tac acc gcc aaa gac tcc
1261 - cgt acc acc gcc gaa acc ttt cat gcc atg
1291 - tat ccg cgc gtc gac gaa tgg atc tcc gtg
1321 - cgc cgc aag gtc gat ccg ctg cgc gta ttc
1351 - gcc tcc gac atg gcc cga cgc ttg gag ctg
1381 - ctg tag
```

EFFECTIVE NEW DRUG TARGET FOR THE TREATMENT OF TUBERCULOSIS

CROSS REFERENCE TO RELATED APPLICATIONS

The present application is the US national stage of international Application PCT/EP2008/001088 filed on Feb. 13, 2008.

FIELD OF THE INVENTION

The present invention allows a screening method for identifying novel drugs for the treatment of tuberculosis as well as a diagnostic method for identifying clinical strains that are resistant to these novel drugs.

BACKGROUND ART

Tuberculosis (TB) remains the leading cause of mortality due to a single infectious agent, *Mycobacterium tuberculosis*. This pathogen has latently infected a third of the world population. Currently, TB chemotherapy is made up of a cocktail of first- and second-line drugs. The actual TB therapy takes from six to nine months, bringing to significant toxicity and drug resistance. Drug-resistant *M. tuberculosis* strains have frequently been encountered from the time anti-TB drugs were introduced. Indeed, mycobacteria are naturally resistant to most of the commonly used antibiotics due to the unusual cell wall. Moreover, genetic changes are considered for acquired drug resistance. *M. tuberculosis* strains that are resistant to an increasing number of second-line drugs used to treat multidrug-resistant tuberculosis (MDR-TB) are becoming a threat to public health worldwide (1). Consequently, there is an urgent need for new drugs to treat tuberculosis. In particular, we require new drugs having novel mechanisms of action that are active against drug-resistant strains. Accordingly, there is also a pressing need to identify new drug targets (2).

SUMMARY OF THE INVENTION

The present invention is based upon the discovery that the protein Rv3790 from *Mycobacterium tuberculosis*, whose encoding DNA-sequence can be retrieved at the web page genolist.pasteur.fr/TubercuList(TubercuList World-Wide Web Server; Rv3790 gene coordinates: from 4162306 to 4163718), is the target for benzothiazinone drugs, a new class of molecules that appear to be very promising in the treatment of tuberculosis ("New thiazinone derivatives, their preparations and their use as antibacterials", pat. appln. No. PCT/EP2006/004942, in the name of Leibniz Institute for Natural Product Research and Infection Biology e.V.Hans-Knöll-Institute (HKI)).

It has been demonstrated that Rv3790 and Rv3791 proteins work in concert and they are involved in arabinogalactan biosynthesis (3). Arabinogalactan is a fundamental component of mycobacterial cell wall, which covalently binds the outer layer of mycolic acids to peptidoglycan. In particular, both Rv3790 and Rv3791 are important to perform transformation of decaprenyl-P-ribose to decaprenyl-P-arabinose (3). The discovery suggests that benzothiazinone drugs interfere with mycobacterial cell wall biosynthesis. It is noteworthy that both rv3790-rv3791 genes were described as essential by Himar1-based transposon mutagenesis in H37Rv strain (4).

We found that mutations in the C-ter of the Rv3790 protein as well as its over-expression confer high level of resistance to benzothiazinone derivative drugs in *Mycobacterium tuberculosis, Mycobacterium bovis* BCG and *Mycobacterium smegmatis*. The rv3790 wild type and mutated genes, as well as rv3791, have been cloned and overexpressed in *Escherichia coli*.

Rv3790 orthologs sensitive to the benzothiazinone derivatives were found in the following genera: *Nocardia, Rhodococcus* and *Corynebacterium*.

It may be hypothesized that the excellent results obtained in the laboratory evaluation for benzothiazinone derivatives are correlated with the Rv3790-inhibitory action that has been discovered. This evidence can trigger new research on drugs acting against Rv3790 protein. Rv3790 protein and related homologues and particularly orthologs are thus not only optimal targets for drugs belonging to the class of benzothiazinones, but also promising target for the discovery of new drugs to be utilized in fighting infections caused by *Mycobacterium tuberculosis, Mycobacterium leprae, Nocardia, Rhodococcus* and *Corynebacterium*.

Therefore, it is an object of the present invention to provide a method for screening drug candidates for the treatment of tuberculosis by interfering with the arabinogalactan biosynthesis, the said method comprising a step of putting into contact a *Mycobacterium tuberculosis* cell culture over-expressing a protein that performs the transformation of decaprenyl-P-ribose to decaprenyl-P-arabinose and that can be encoded by rv3790 gene or homologues thereof or any open-reading artificial frame whose gene product is identical or homologous to Rv3790 protein, with a drug candidate and then evaluating the percentage of inhibition caused by the drug candidate against a control (*M. tuberculosis* transformed with pSODIT-2 vector alone) in an assay test.

Preferably, the assay test is an in vitro assay test of antibacterial activity or an enzymatic test.

Another object of the present invention is a cell culture preparation from *Mycobacterium tuberculosis* mutant strains (having the amino acid cysteine in the 387 position substituted by a serine or a glycine) to be used as a control tool in the method of the present invention.

A further object of the present invention is the preparation of recombinant Rv3790 protein in the wild type and mutated forms for enzymatic activity assay and screening method for identifying novel drugs.

The discovery that Rv3790-type proteins encoded by mutated genes are responsible for resistance to drugs interfering with the arabinogalactan biosynthesis, such as benzothiazinone drugs, will have important implications in the diagnosis and treatment of drug-resistant mycobacterial strains.

It is thus another object of the present invention to provide a rapid diagnostic method for drug-resistant mycobacterial strains that involves amplification by Polymerase Chain Reaction (5) of an internal region of rv3790 gene from a *Mycobacterium tuberculosis* strain isolated from a TB patient, overlapping the 387 codon, and analysing the DNA sequence for the presence of the identified mutations as responsible for resistance to drugs interfering with arabinogalactan biosynthesis, such as benzothiazinones.

In the context of the present invention, the term "drug interfering with the arabinogalactan biosynthesis" means a molecule that prevents the transformation of decaprenyl-P-ribose to decaprenyl-P-arabinose by blocking or silencing a protein that performs the transformation of decaprenyl-P-ribose to decaprenyl-P-arabinose and that can be encoded by rv3790 gene or homologues thereof or any open-reading artificial frame whose gene product is identical or homologous to Rv3790 protein.

Another object of the present invention are inhibitors of Rv3790 protein obtained by the screening method of the invention, as well as a method of treatment of tuberculosis by using such inhibitors, wherein such inhibitors are preferably selected from benzothiazinones (or other molecules whose metabolism produce benzothiazinones), monoclonal antibodies raised against Rv3790, antisense RNA sequences or vaccines.

BRIEF DESCRIPTION OF THE DRAWINGS

FIG. 1 shows a multi-alignment analysis with Rv3790 orthologs from several genera belonging to actinobacteria;

FIG. 2 shows the DNA sequence of rv3790 gene.

DETAILED DESCRIPTION OF THE INVENTION

A first object of the present invention is a method for screening drug candidates for the treatment of tuberculosis by interfering with the arabinogalactan biosynthesis, the said method comprising a step of putting into contact a *Mycobacterium tuberculosis* cell culture (transformed with pSODIT-2/Rv3790) over-expressing a protein that performs the transformation of decaprenyl-P-ribose to decaprenyl-P-arabinose and that can be encoded by rv3790 gene or homologues thereof or any open-reading artificial frame whose gene product is identical or homologous to Rv3790 protein, with a drug candidate and then evaluating the percentage of inhibition caused by the drug candidate against a control in an assay test.

Preferably, the said assay test is an in vitro test for antibacterial activity or an enzymatic test.

In the antibacterial test, the evaluation of the percentage of inhibition is preferably performed by determining the Minimum Inhibitory Concentrations (MICs). MICs are defined as the lowest concentration of an antimicrobial that will inhibit the visible growth of a microorganism after suitable incubation.

Each drug candidate is also tested on a cell culture of *M. tuberculosis* transformed with pSODIT-2 vector alone.

As a control, isoniazid can be used, this being the reference drug in the treatment of tuberculosis.

Alternatively or in addition, a different control experiment can be run, wherein no drug candidate treatment is made, so that a 0% inhibition is given. The % inhibition obtained with the drug candidate with respect to such a control is evaluated.

The said step of putting into contact a *Mycobacterium tuberculosis* cell culture with a drug candidate can be performed by putting the cell preparation onto one or more solutions of the drug candidate at different concentrations of drug, in a suitable medium.

The drug candidate is usually tested in a suitable form that allows good contact between the substance and the cell culture. Preferably, the drug candidate is utilized in solution or suspension. The drug candidate is used in amounts or concentrations that depend on several factors, among which the molecular weight of the substance, its solubility and so on.

Preferably, two or more concentrations of drugs are used, in order to calculate the MIC (Minimal Inhibitory Concentration) for each candidate.

Preferably, the suitable medium is Middlebrook 7H11 solid medium (Difco supplier). More preferably, this medium is supplied with oleic acid, bovine serum albumin, dextrose and catalase (OADC). This medium is typical for mycobacterial strains.

A further object of the present invention is the preparation of recombinant Rv3790 protein in the wild type and mutated forms from *Escherichia coli* cells for enzymatic activity assay (according to the method described in reference 3) and a screening method for identifying novel drugs. The enzymatic screening test can be performed by using the recombinant Rv3790 enzyme in a reaction mixture containing FAD, $NAD^+$, NADPH, and radiolabelled decaprenylphosphoryl ribose (DPR) that through the enzymatic reaction is transformed into Decaprenylphosphoryl-D-Araf (DPA). This is the control experiment. Another experiment is run, wherein the procedure is repeated in the presence of the drug candidate. The amount of the so formed DPA is detected and the % inhibition of the enzymatic reaction caused by the drug candidate is calculated. The formation of DPA is monitored according to standard procedures well known to the skilled man, such as those described in reference (3).

The inventive screening method may also comprise an in vivo evaluation of the activity of the drug candidates that pass the in vitro screening step. This in vivo evaluation can be performed as described below, in particular by administering preselected dosage regimens of the drug candidate to mice hematogeneously disseminated with a tuberculosis strain, against a control drug and against a placebo.

The control drug is preferably isoniazid.

Preferably, BALB/c line mice are used.

Preferably, the tuberculosis strain is a virulent culture of *Mycobacterium tuberculosis* H37Rv, more preferably at a dose of $5 \times 10^6$ CFU (Colony Forming Unit) in saline buffer.

The screening dose of the drug candidate can vary in a wide range of doses depending on several factors, such as the MIC calculated from the above in vitro test results or the $LD_{50}$ that can be determined for such compound. Generally, the dose of the drug candidate used in the present in vivo screening method will be below its $LD_{50}$.

Preferably, the drugs are introduced orally as suspension in a suitable buffer.

Preferably, the treatment is administered daily 6 times per week.

To determine the efficacy of each treatment regimen, macroscopical changes in parenchymal organs of the mice, growth of mycobacteria from pathologic material on solid media, as well as a bacterioscopical index of organ injury are recorded. A qualitative and quantitative analysis of macroscopical changes in the liver, spleen and lungs is also carried out and an injury index (using a four-score scale) is calculated.

A diagnostic method for drug-resistant mycobacterial strains is also provided as a further object of the present invention. The diagnostic method involves amplification by Polymerase Chain Reaction (5) of rv3790 gene from a *Mycobacterium tuberculosis* strain isolated from a TB patient and analysis of DNA sequence for the presence of the identified mutations.

Preferably, the method comprises amplification by Polymerase Chain Reaction (5) of an internal region of rv3790 gene from a *Mycobacterium tuberculosis* strain isolated from a TB patient, overlapping the 387 codon, and analysis of DNA sequence for the presence of the identified mutations (cysteine versus glycine or cysteine versus serine) as responsible for resistance to drugs interfering with arabinogalactan biosynthesis, such as benzothiazinones.

Another object of the present invention are inhibitors of Rv3790 protein obtainable by the screening method of the invention, as well as a method of treatment of tuberculosis by using such inhibitors, wherein such inhibitors are preferably selected from benzothiazinones (or molecules whose metabolism produce benzothiazinones), monoclonal antibodies raised against to Rv3790, antisense RNA sequences or vaccines.

Drugs Interfering with the Arabinogalactan Biosynthesis

The drugs obtainable through the screening method of the invention are preferably selected among monoclonal antibodies against Rv3790 protein and mRNA antisense sequences for rv3790 gene, such drugs displaying a % inhibition greater than 50% in the in vitro screening test and/or a % inhibition greater than 50% in the anti-bacterial in vivo test of the invention.

In a preferred embodiment of the present invention, the said drugs are monoclonal antibodies against Rv3790 protein. Such antibodies can be obtained according to conventional procedures as well described in literature (6, 7).

In a further embodiment of the present invention, the said drugs are rv3790 gene antisense sequences.

The present invention provides antisense oligomers having a sequence effective to inhibit or block the expression of the rv3790 encoding gene or mRNA sequence. Antisense technology, which uses specific-oligonucleotides to inhibit expression of target gene products, is developing as a therapeutic modality for human disease. Several selection criteria are available to contribute to the optimization of antisense oligonucleotide antagonists. For example, it is advisable to choose sequences with 50% or more GC content. Preferred sequences span the AUG initiation codon of the target protein, but sites in the coding region and 5'UTR may perform equally well. Such sequences are generally about 18-30 nucleotides long. Longer oligomers are often found to inhibit the target to a greater extent, indicating that a preferred length is about 25 mer for the first oligonucleotides chosen as antisense reagents. Typically, three oligonucleotide sequences are chosen with regard to these criteria, and compared for antagonist activity to control oligonucleotide sequences, such as "reverse" oligonucleotides or those in which about every fourth base of the antisense sequence is randomized. Therefore, a preferred sequence for making antisense oligomer sequences to rv3790 is a 25 mer sequence from the rv3790 mRNA sequence: AUG UUG AGC GUG GGA GCU ACC ACU A (SEQ ID. No.:1). The whole sequence of the rv3790 gene is deposited in genolist.pasteur.fr/TuberculList/under gene name rv3790. The entire rv3790 DNA sequence is reported in FIG. 2. as SEQ ID. NO.:2. Such preferred sense sequences are used to construct antisense oligonucleotide agents (and suitable controls) for an in vitro comparison as inhibitors of Rv3790 protein. These in vitro data are predictive of human clinical utility using antisense agents of comparable design.

In a still further embodiment, vaccines constituted by or including the Rv3790 protein sequence can also be provided.

Method of Treatment

The present invention further encompasses a method of treatment of a patient affected by tuberculosis, the method including administering to the said patient an antibacterial effective amount of a drug interfering with the arabinogalactan biosynthesis by blocking or silencing a protein that performs the transformation of decaprenyl-P-ribose to decaprenyl-P-arabinose.

Preferably, the said drug is a benzothiazinone molecule or monoclonal antibodies against Rv3790 protein or mRNA antisense sequences for rv3790 gene.

Preferably, the method of treatment further includes administering an antibacterial drug against *Mycobacterium tuberculosis* having a different mechanism of action, such as isoniazid.

The dose of the said drug interfering with the arabinogalactan biosynthesis that is administered can vary in a wide range of doses, depending on inhibitor's activity, the seriousness of the disease, the conditions of the patient, its weight and age as well as the route of administration, as will be determined by the clinician.

Generally, the drug can be used in doses ranging from 0.001 mg to 50 mg per kg of body weight, from 1 to 4 times a day.

The use of a drug interfering with the arabinogalactan biosynthesis as defined above, for the preparation of a medicament for treating tuberculosis is also claimed.

Experimental Part

Determination of the In Vitro Minimum Inhibitory Activity (MIC) of a Drug Candidate Against Mycobacteria A single colony of *M. tuberculosis* strain is used to inoculate Middlebrook 7H9 enriched with 10% OADC and 0.05% Tween 80 (Difco). This medium is typical for mycobacterial strains.

The culture is incubated at 37° C. until it reaches exponential growth phase ($OD_{600}$ nm=~$10^8$ CFU/ml). Dilutions of such culture are prepared and used to plate ~$10^5$ CFU.

Mic Evaluations on Solid Media

Middlebrook 7H11 (Difco) agar plates containing 10% OADC are prepared by adding increasing amounts of drugs. Preferably, several concentrations of drugs are used, in order to calculate the MIC for each candidate. Culture dilutions are plated onto media and plates are incubated at 37° C. for 21 days. Growth inhibition is visually evaluated.

Determination of the in vivo inhibitory activity of drug candidates against *Mycobacterium tuberculosis* in the murine TB model To determine the chemotherapeutic efficacy, BALB/c line mice with experimental hematogenously disseminated tuberculosis can be used.

The mice are infected with a 2-week virulent culture of *Mycobacterium tuberculosis* H37Rv by intravenous injection (into tail vein) of the mycobacterial suspension at a dose of 5×$10^6$ CFU (Colony-Forming-Unit) in 0.5 ml saline. All the experimental animals are divided into groups depending on the treatment regimen used.

Treatment is started the next day after infection. The drugs are introduced orally as suspension in carboxymethylcellulose/water with a small quantity PEG-400. Chemotherapy is administered daily 6 times per week.

The animals are then sacrificed. To determine the efficacy of each treatment regimen, macroscopical changes in parenchymal organs of the mice, growth of mycobacteria from pathologic material on solid media, as well as a bacterioscopical index of organ injury are recorded. A qualitative and quantitative analysis of macroscopical changes in the liver, spleen and lungs is also carried out and an injury index (using a four-score scale) is calculated.

Macroscopical evaluation of the efficacy of each treatment regimen is expressed in the efficacy index, calculated using the following formula:

Efficacy index=100%−Injury index of the studied group/Injury index of the control group×100

Microbiological examination includes culture for determination of CFU in parenchymal organs. For this purpose, the right lung and separately the spleen are homogenized with 6% sulfuric acid, centrifuged, washed by water and saline. The yield (about 0.5 mL) is diluted by 1.0 mL of saline and homogenized. This suspension (0.5 mL) of test organs is diluted 100 and 1000 times by saline and is distributed on solid Finn-2 medium. The cultures are incubated at 37° C. for 1 month and read weekly starting from day 10. After 28 days CFU's are counted.

Preparation of Recombinant Rv3790

In order to obtain protein expression into *E. coli*, several growth conditions were tested, with or without isopropyl-β-thiogalactoside (IPTG) as inductor, at concentrations ranging between 0.125 mM e 1 mM. All cultures had been incubated at 37° C. for 2 hours, at 27° C. for 2 and 4 hours and at 20° C. for 2 and 20 hours. Cells were harvested by centrifugation and derived protein extracts were analyzed by SDS-PAGE run. Recombinant proteins were purified according to supplier's instructions (Qiagen).

Determination of Rv3790 as a Target for Benzothiazionones

In order to identify the molecular target for benzothiazinones, two different scientific/technical approaches have been followed:
a) Transformation of *Mycobacterium smegmatis* cosmid library into *M. smegmatis* and selection for resistance to benzothiazinones;
b) Conventional mutagenesis: searching for spontaneous mutations by plating mycobacterial cultures onto media containing benzothiazinones.

The minimal inhibitory concentration (MIC) of different benzothiazinones, for *M. smegmatis* mc²155, *M. bovis* BCG and *M. tuberculosis* H37Rv was determined as described above on Middlebrook 7H11, as solid medium, supplemented with oleic acid, bovine serum albumin, dextrose and catalase (OADC).

Attention was focused on the most active benzothiazinone: 10526038. MIC determination was carried out also for isoniazid as control compound. MIC values of 10526038 and isoniazid are shown in Table 1.

TABLE 1

MICs of 10526038 and isoniazid for different mycobacterial species.

| Strains | MIC values | |
|---|---|---|
|  | 10526038 [ng/ml] | Isoniazid [µg/ml] |
| *M. smegmatis* mc²155 | 4 | 16 |
| *M. bovis* BCG | 2 | 0.05 |
| *M. tuberculosis* H37Rv | 0.75 | 0.05 |

Approach a)

A genomic library of *M. smegmatis* mc²155 was constructed by using pYUB18 cosmid vector and transformed into *M. smegmatis* mc²155; recombinant clones were selected by plating onto different concentrations of benzothiazinones (ranging from 16 ng/ml to 64 ng/ml). Two cosmids, responsible for benzothiazinone resistance (8×-MIC), were selected, partially sequenced and compared with the *M. smegmatis* genome sequence (www.tiger.org). These cosmids showed a 22 kb overlapping insert. By subcloning experiments of the common genomic region, a gene responsible for 10526038 resistance was identified. This 1383 bp gene encodes a hypothetical oxidoreductase (MSMEG_6382) which is highly homologous to Rv3790 of *M. tuberculosis* (web page genolist.pasteur.fr/TuberculList/). It has been demonstrated that Rv3790 and Rv3791 proteins work in concert and they are involved in arabinogalactan biosynthesis, a fundamental component of mycobacterial cell wall. They both are important to perform transformation of decaprenyl-P-ribose to decaprenyl-P-arabinose (3).

It is noteworthy that both rv3790-rv3791 genes were described as essential for the life of *M. tuberculosis* by Himar1-based transposon mutagenesis in H37Rv strain (4). The rv3790 gene was cloned into pSODIT-2 expression vector and transformed into the following strains: *M. smegmatis*, *M. bovis* BCG and *M. tuberculosis*. As shown in Table 2, the overexpression of Rv3790 confers high level of resistance to 10526038 in all three mycobacterial species.

TABLE 2

MICs to 10526038 of different mycobacterial species over-expressing Rv3790.

| | MIC 10526038 (resistance level) | | |
|---|---|---|---|
| Plasmid | *M. smegmatis* [ng/ml] | *M. bovis* BCG [ng/ml] | *M. tuberculosis* [ng/ml] |
| pSODIT2 | 4 | 2 | 0.75 |
| Rv3790/pSODIT-2 | 256 (32X-MIC) | 32 (8X-MIC) | 500 (333X-MIC) |

Approach b)

Spontaneous resistant mutants were isolated, respectively, in *M. smegmatis*, *M. bovis* BCG and *M. tuberculosis*.

Results Obtained in *M. smegmatis* mc²155

In order to identify the cellular target for benzothiazinones, *M. smegmatis* mc²155 mutants resistant to benzothiazinone 10526038 were isolated by spontaneous conventional mutagenesis by plating ~$10^{10}$ cells onto solid media containing different concentrations of the compound, ranging from 10 to 30 fold the MIC of the wild type strain. Resistant mutants were isolated at a frequency ranging from $10^{-7}$ to $10^{-9}$. The results of this selection are shown in Table 3.

TABLE 3

*M. smegmatis* spontaneous mutants resistant to 10526038.

| *M. smegmatis* mutants | 10526038 concentration utilized for isolation | Isolation frequency | Resistance level |
|---|---|---|---|
| MN 47; 48 | 30X-MIC | $5 \cdot 10^{-9}$ | 500X-MIC |
| MN 81; 84 | 30X-MIC | $5 \cdot 10^{-9}$ | ≥4000X-MIC |

MSMEG_6382 gene and a 200 bp upstream region were sequenced in the 4 *M. smegmatis* mutants (MN47, MN48 and MN81, MN84) with a different level of 10526038 resistance (500/>4000X-MIC). Such nucleotide region was compared to wild type sequence (www.tiger.org). Two point mutations were identified in the nucleotide sequences from *M. smegmatis* resistant strains. The two mutations are localized into the same codon, but on different nucleotides, according to different level of resistance, as shown in Table 4.

TABLE 4

Mutations identified in *M. smegmatis* resistant strains.

| *M. smegmatis* strains | MIC (Resistance Level) | Codon | Amino acid (394) |
|---|---|---|---|
| Wild type | 4 ng/ml | Tgc | Cysteine |
| Mutant MN47, MN48 | 4 µg/ml (500X-MIC) | Ggc | Glycine |
| Mutant MN81, MN84 | >16 µg/ml (>4000X-MIC) | Tcc | Serine |

Mutated nucleotide is underlined.

Results Obtained in *M. bovis* BCG Pasteur

In order to identify the cellular target for benzothiazinones, *M. bovis* BCG high resistant mutants were isolated by plating ~$10^{10}$ cells onto solid media containing different concentrations of 10526038, ranging from 5 to 40 fold the MIC of the wild type strain. Resistant mutants were obtained at a frequency of $10^{-8}$. The result of this selection is shown in Table 5.

TABLE 5

Spontaneous *M. bovis* mutants resistant to 10526038.

| *M. bovis* mutants | 10526038 concentration utilized for isolation | Isolation frequency | Resistance level |
|---|---|---|---|
| BN1-8 | 40X-MIC | $1.8 \cdot 10^{-8}$ | ≥8000X-MIC |

Sequencing of the rv3790 homologous gene was performed in the eight *M. bovis* mutants. A point mutation was identified into the corresponding codon mutated in *M. smegmatis*. In all 8 mutants, the second nucleotide was mutated, changing the amino acid from the wild type cysteine to a serine, as shown in Table 6.

TABLE 6

Mutations identified in *M. bovis* resistant strains.

| *M. bovis* strains | MIC (Resistance Level) | Codon | Amino acid (387) |
|---|---|---|---|
| Wild type | 2 ng/ml | Tgc | Cysteine |
| Mutant BN1-8 | >16 μg/ml (≥8000X-MIC) | Tcc | Serine |

Mutated nucleotide is underlined.

Results Obtained in *M. tuberculosis* H37Rv

To find the target of benzothiazinones in *M. tuberculosis* (Mtb), we have isolated some Mtb spontaneous resistant mutants. The MIC value of 10526038 in Mtb is very low, 1.5 ng/ml (versus 0.05 μg/ml of isoniazid).

The isolation of resistant mutants was performed onto 7H11 medium (typical for mycobacteria) with the addition of 10526038 drug at different concentrations. Four independent Mtb cultures have been used at O.D.$_{600}$=1. Aliquots (250 μl) of the four cultures were plated onto the following concentration of drugs: 10X MIC, 40X MIC, 70X MIC, 150X MIC, and 300X MIC. We obtained Mtb spontaneous resistant mutants at all concentrations of drugs with the exception of 10X MIC. In Table 7 are shown the isolated mutants, the frequency, and the MIC values.

TABLE 7

Mtb spontaneous mutants resistant to 10526038.

| Mtb mutants | 10526038 concentration utilized for isolation | Isolation frequency | Resistance level |
|---|---|---|---|
| NTB1 | 150X MIC | $6.6 \cdot 10^{-7}$ | ≥2000X MIC |
| NTB2 | 300X MIC | $2 \cdot 10^{-8}$ | ≥2000X MIC |
| NTB3 | 300X MIC | $2 \cdot 10^{-8}$ | ≥2000X MIC |
| NTB4 | 300X MIC | $2 \cdot 10^{-8}$ | ≥2000X MIC |
| NTB5 | 300X MIC | $2 \cdot 10^{-8}$ | ≥2000X MIC |
| NTB6 | 300X MIC | $2 \cdot 10^{-8}$ | ≥2000X MIC |
| NTB7 | 300X MIC | $2 \cdot 10^{-8}$ | ≥2000X MIC |
| NTB8 | 40X MIC | $3.3 \cdot 10^{-7}$ | ≥2000X MIC |
| NTB9 | 70X MIC | $3.3 \cdot 10^{-7}$ | 166X MIC |
| NTB10 | 150X MIC | $6.6 \cdot 10^{-7}$ | ≥2000X MIC |

It is important to underline that the mutants have been isolated only onto high drug concentrations and that the isolated mutants have two different levels of resistance. Particularly, NTB9 mutant is less resistant and grows very slowly.

We sequenced the rv3790 gene in all the mutants to find the mutation responsible for resistance. Two different missense point mutations mapping in the same codon of rv3790 gene were found (Table 8).

TABLE 8

Mutations identified in Mtb Rv3790 resistant strains.

| Mtb strains | MIC values | Codon | Amino acid (387 position) |
|---|---|---|---|
| Mtb wild-type | 1.5 ng/ml | tgc | Cysteine |
| NTB1-8, NTB10 mutants | ≥2000X-MIC | tcc | Serine |
| NTB9 mutant | 166X-MIC | ggc | Glycine |

Mutated nucleotide is underlined.

The above results point to Rv3790 protein as a target for benzothiazinone drugs.

Since two common antibiotic resistance mechanisms include target amplification, or target modification, with the first method we isolated mycobacterial strains resistant to benzothiazinones via amplification mechanism, while with the second one we isolated mycobacterial strains resistant to benzothiazinones through mutations in a specific codon of rv3790 gene. This codon is present in the C-terminal portion of the Rv3790 protein; a Cysteine in the wild type Rv3790 protein changes into a Glycine in *M. tuberculosis* and *M. smegmatis* (see NTB9, MN47 and MN48 mutants) or Serine in *M. tuberculosis, M. bovis* BCG and *M. smegmatis* (see NTB1-8, NTB10, BN1-8, MN81, and MN84 mutants) giving different levels of resistance. The highest level of resistance was observed with Serine substitution.

As all mutations are present in the same codon, the cystein could be the active site for the binding with the drug.

Therefore, mutants selected in vitro strongly suggest that the benzothiazinone drugs target the Rv3790 protein, thus affecting arabinogalactan biosynthesis.

Rv3790 Orthologues

By BLAST program (web page www.ncbi.nlm.nih.gov/sutils/genom$_{13}$ table.cgi?organism=microb) we searched for the presence of rv3790 orthologs in related microorganisms belonging to actinomycetes family: *Mycobacterium avium, Mycobacterium aurum, Mycobacterium leprae*, other mycobacterial species, *Nocardia* sp., *Rhodococcus* sp. and *Corynebacterium* spp. As the rv3790 DNA sequence was not available for some microorganisms, such as *Mycobacterium aurum*, we cloned and sequenced in our laboratory the corresponding gene. The Rv3790 protein is well conserved in all microorganisms tested as demonstrated by multi-alignment analysis with ClustalW program (npsa-pbil.ibcp.fr/cgi-bin/npsa$_{13}$ automat.pl?page=/NPSA/npsa$_{13}$ clustalw.html).

It is noteworthy the conservation of the critical cysteine through the tested microorganisms. Indeed, we found a high conservation of Cysteine in these microorganisms, with the exception of *Mycobacterium avium, Mycobacterium avium paratuberculosis*, and *Mycobacterium aurum* where Cys is substituted by alanine and serine, respectively (FIG. 1).

To verify if the absence of cysteine confers resistance to 10526038 benzothiazinone, we performed the MIC evaluations for the following microrganisms: *Mycobacterium avium, Mycobacterium aurum, Nocardia* spp., *Rhodococcus* spp. and *Corynebacterium* spp.

For mycobacteria species the experiment was carried out onto 7H11 medium with different drug concentrations. The MICs were determined from a culture dilution at 0.5 Macfarland.

For the other actinomycetes *Nocardia* spp., *Rhodococcus* sp. and *Corynebacterium* sp, the dilutions at 0.5 Macfarland were streaked onto blood-Mueller Hinton agar with the addition of different drug concentrations.

As shown in Table 9, 10526038 benzothiazinone is more active against the actinomycetes species. Only *M. avium* and *M. aurum* appear naturally resistant to benzothiazinones; thus confirming our hypothesis that Cys plays a key role in 10526038 benzothiazinone sensitivity.

TABLE 9

MIC evaluations of 10526038 benzothiazinone in actinomycetes species.

| Microorganisms | N386 MIC value |
| --- | --- |
| *Mycobacterium tuberculosis* | 0.75 ng/ml |
| *Mycobacterium bovis* BCG | 1.5 ng/ml |
| *Mycobacterium smegmatis* | 4 ng/ml |
| *Mycobacterium aurum* DSM43999 | >50 μg/ml |
| *Mycobacterium aurum* DSM43536 | >50 μg/ml |
| *Mycobacterium aurum* SB66 clinical isolate | >50 μg/ml |
| *Mycobacterium vaccae* | 0.75 ng/ml |
| *Mycobacterium avium* clinical isolate | >25 μg/ml |
| *Nocardia* spp. clinical isolate | 12 ng/ml |
| *Rhodococcus* spp. clinical isolate | 6 ng/ml |
| *Corynebacterium* spp. clinical isolate | among 200-500 ng/ml |

Heterologous Expression of Rv3790

As Rv3790 protein work in concert with Rv3791 (3) the following recombinant clones have been constructed:

1) Rv3790 WT enzyme has been produced into *Escherichia coli* BL21(DE3)pLysS by using pET32 vector.
2) Rv3791 WT enzyme has been produced into *Escherichia coli* BL21(DE3)pLysS by using pET15 vector.
3) Rv3790 mutated enzyme (Cys→Gly: from *M. tuberculosis* resistant mutant) has been produced into *Escherichia coli* BL21(DE3)pLysS by using pET32 vector.
4) Rv3790 mutated enzyme (Cys→Ser: from *M. tuberculosis* resistant mutant) has been produced into *Escherichia coli* BL21(DE3)pLysS by using pET32 vector.

rv3790 and rv3791 genes from *M. tuberculosis* wild type and resistant strains (NTB1 and NTB9) were amplified from *M. tuberculosis* genome by polymerase chain reaction (PCR) and cloned into the different expression vectors. The recombinant constructs were transformed into *E. coli* BL21DE3/pLysS cells, by electroporation. In order to obtain protein expression into *E. coli*, several growth conditions were tested, with or without isopropyl-β-thiogalactoside (IPTG) as inductor, at concentrations ranging between 0.125 mM e 1 mM. All cultures had been incubated at 37° C. for 2 hours, at 27° C. for 2 and 4 hours and at 20° C. for 2 and 20 hours. Cells were harvested by centrifugation and derived protein extracts were analyzed by SDS-PAGE run.

References

1. Shah N S, Wright A, Bai G H, et al. Worldwide emergence of extensively drug-resistant tuberculosis. *Emerg Infect Dis* 2007, 13:380-387.
2. Williams K J, Duncan K. Current strategies for identifying and validating targets for new treatment-shortening drugs for TB. *Curr Mol Med* 2007, 7:297-307
3. Mikusova K, et al. Decaprenylphosphoryl arabinofuranose, the donor of the D-arabinofuranosyl residues of mycobacterial arabinan, is formed via a two-step epimerization of decaprenylphosphoryl ribose. *J Bacteriol* 2005, 187:8020-8025.
4. Sassetti C M, et al. Genetic requirements for mycobacterial survival during infection. *Proc Natl Acad Sci USA* 2003 100:12989-12994.
5. Mullis K, et al. Specific enzymatic amplification of DNA in vitro: the polymerase chain reaction. *Cold Spring Harb Symp Quant Biol* 1986, 51:263-73.
6. Andersen P, et al. Recall of long-lived immunity to *Mycobacterium tuberculosis* infection in mice. *J Immunol* 1995, 154:3359-3372.
7. Kohler G, Milstein C. Continuous cultures of fused cells secreting antibody of predefined specificity. *Nature* 1975, 256:495-497.

The invention claimed is:

1. A method for screening in vitro drug candidates for treatment of tuberculosis, the treatment performed by interfering with arabinogalactan biosynthesis, the method comprising putting into contact a *Mycobacterium tuberculosis* cell culture with a drug candidate, the *Mycobacterium tuberculosis* cell culture over-expressing a protein that performs transformation of decaprenyl-P-ribose to decaprenyl-P-arabinose;

detecting inhibition of the *Mycobacterium tuberculosis* cell culture in an assay test following the putting into contact;

determining a percentage inhibition of the *Mycobacterium tuberculosis* cell culture by comparing the detected inhibition in the *Mycobacterium tuberculosis* cell culture against a control in the assay test; and determining if the percentage inhibition is actually due to interfering with arabinogalactan biosynthesis.

2. The method of claim 1, wherein the protein that performs transformation of decaprenyl-P-ribose to decaprenyl-P-arabinose is encoded by an rv3790 gene an homologue thereof or an open-reading artificial frame encoding a protein identical or homologous to an Rv3790 protein.

3. The method of claim 2, wherein the *Mycobacterium tuberculosis* cell culture over-expressing a protein that performs transformation of decaprenyl-P-ribose to decaprenyl-P-arabinose is obtained by transforming a *Mycobacterium tuberculosis* cell culture with pSODIT-2/Rv3790.

4. The method of claim 1, wherein putting into contact a *Mycobacterium tuberculosis* cell culture with a drug candidate is performed by plating a cell preparation onto a suitable medium containing different concentrations of the drug candidate.

5. The method of claim 4, wherein the suitable medium is Middlebrook 7H11 solid medium (Difco supplier).

6. The method of claim 5, wherein the suitable medium is supplied with oleic acid, bovine serum albumin, dextrose and catalase (OADC).

7. The method of claim 1, wherein the assay test is an in vitro antibacterial test.

8. An enzymatic test for screening in vitro drug candidates for treatment of tuberculosis comprising:
putting into contact a drug candidate with a recombinant Rv3790 enzyme in a reaction mixture containing FAD, NAD+, NADPH and radiolabelled decaprenylphosphoryl ribose (DPR) to provide an enzymatic reaction resulting in production of decaprenylphosphoryl-d-Araf (DPA); and
determining the percentage of inhibition of production of decaprenylphosphoryl-d-Araf (DPA) by the recombinant Rv3790 enzyme following the putting into contact to select the drug candidate for treatment of tubercolosis,
wherein the protein that performs transformation of decaprenyl-P-ribose to decaprenyl-P-arabinose is encoded by an rv3790 gene, an homologue thereof or by an open-reading artificial frame encoding a protein identical or homologue to an Rv3790 protein.

9. The method of claim 1, wherein determining the percentage inhibition is performed by determining a Minimum Inhibitory Concentration (MIC) of the drug candidate.

10. The method of claim 9, wherein the Minimum Inhibitory Concentration is calculated by using two or more drug concentrations for each drug candidate.

11. The method of claim 9, wherein the control is isoniazid.

12. The method of claim 1, wherein the control is a *Mycobacterium tuberculosis* cell culture not treated with a drug candidate.

13. The method of claim 1, further comprising testing each drug candidate on a m*Mycobacterium tuberculosis* cell culture transformed with a pSODIT-2 vector alone.

14. The method of claim 1, wherein the assay test is an in vitro assay test, the method further comprising
performing an in vivo screening evaluation of the drug candidates that pass the in vitro test, wherein the in vivo evaluation is performed by
administering a preselected dosage regimen of the drug candidate that pass the in vitro test, a control drug, and a placebo to mice hematogeneously disseminated with a tuberculosis strain, and
detecting inhibition of tuberculosis in the mice hematogeneously disseminated with a tuberculosis strain following the administering.

15. The method of claim 14, wherein the control drug is isoniazid.

16. The method of claim 14, wherein the mice are BALB/C mice.

17. The method of claim 14, wherein the tuberculosis strain is a virulent culture of *Mycobacterium tuberculosis* H37Rv.

18. A diagnostic method for identifying drug-resistant mycobacterial strains in a patient, the method comprising
amplifying an rv3790 gene from a *Mycobacterium tuberculosis* strain isolated from the patient and
analyzing the DNA sequence for presence of predetermined mutations, the predetermined mutations associated to a resistance of *Mycobacterium tuberculosis* to benzothiazinones, wherein the predetermined mutations are cysteine versus glycine or cysteine versus serine at codon 387 of SEQ ID NO: 2 of the rv3790 gene.

19. A bacterial cell culture from a *Mycobacterium tuberculosis* mutant strain, the cells of the culture comprising a rv3790 gene sequence of SEQ ID NO: 2 and/or a protein encoded thereby, wherein an amino acid cysteine encoded by codon 387 of SEQ ID NO: 2 is substituted by a serine or a glycine.

20. A method of treatment of a patient affected by tuberculosis, the method comprising
administering to the patient an antibacterial effective amount of a drug interfering with arabinogalactan biosynthesis, the interfering obtained by blocking a protein that performs transformation of decaprenyl-P-ribose to decaprenyl-P-arabinose.

21. The method of claim 20, wherein the drug is a benzothiazinone molecule or monoclonal antibodies against Rv3790 protein or mRNA antisense sequences for rv3790 gene.

22. The method of claim 20, further including administering an antibacterial drug against *Mycobacterium tuberculosis* having a mechanism of action different from interfering with arabinogalactan biosynthesis, the interfering obtained by blocking a protein that performs transformation of decaprenyl-P-ribose to decaprenyl-P-arabinose.

* * * * *

UNITED STATES PATENT AND TRADEMARK OFFICE
CERTIFICATE OF CORRECTION

PATENT NO.        : 9,128,088 B2
APPLICATION NO.   : 12/867049
DATED             : September 8, 2015
INVENTOR(S)       : Giovanna Riccardi et al.

Page 1 of 1

It is certified that error appears in the above-identified patent and that said Letters Patent is hereby corrected as shown below:

Item (73) (Assignee), please delete "UNIVERSITA' DEGLI STUDI DI PAVIA (IT)"
and replace with "SENTINEL CH S.P.A (IT)".

Signed and Sealed this
Twenty-eighth Day of June, 2016

Michelle K. Lee
*Director of the United States Patent and Trademark Office*

SEQUENCE LISTING

```
<160> NUMBER OF SEQ ID NOS: 19

<210> SEQ ID NO 1
<211> LENGTH: 25
<212> TYPE: RNA
<213> ORGANISM: Mycobacterium tuberculosis

<400> SEQUENCE: 1
auguugagcg ugggagcuac cacua                                            25

<210> SEQ ID NO 2
<211> LENGTH: 1386
<212> TYPE: DNA
<213> ORGANISM: Mycobacterium tuberculosis

<400> SEQUENCE: 2
atgttgagcg tgggagctac cactaccgcc acccggctga ccgggtgggg ccgcacagcg      60
ccgtcggtgg cgaatgtgct tcgcacccca gatgccgaga tgatcgtcaa ggcggtggct     120
cgggtcgccg agtcgggggg cggccggggt gctatcgcgc gcgggctggg ccgctcctat     180
```

```
gggggacaacg cccaaaacgg cggtgggttg gtgatcgaca tgacgccgct gaacactatc      240
cactccattg acgccgacac caagctggtc gacatcgacg ccggggtcaa cctcgaccaa      300
ctgatgaaag ccgccctgcc gttcgggctg tgggtcccgg tgctgccggg aacccggcag      360
gtcaccgtcg gcggggcgat cgcctgcgat atccacggca agaaccatca cagcgctggc      420
agcttcggta ccacgtgcg cagcatggac ctgctgaccg ccgacggcga gatccgtcat      480
ctcactccga ccggcgagga cgccgaactg ttctgggcca ccgtcggggg caacggtctc      540
accggcatca tcatgcgggc caccatcgag atgacgccca cttcgacggc gtacttcatc      600
gccgacggcg acgtcaccgc cagcctcgac gagaccatcg ccctgcacag cgacggcagc      660
gaagcgcgct acacctattc cagtgcctgg ttcgacgcga tcagcgctcc cccgaagctg      720
ggccgcgcgg cggtatcgcg tggccgcctg gccaccgtcg agcaattgcc tgcgaaactg      780
cggagcgaac ctttgaaatt cgatgcgcca cagctactta cgttgcccga cgtgtttccc      840
aacgggctgg ccaacaaata taccttcggc ccgatcggcg aactgtggta ccgcaaatcc      900
ggcacctatc gcggcaaggt ccagaacctc acgcagttct accatccgct ggacatgttc      960
ggcgaatgga accgcgccta cggcccagcg ggcttcctgc aatatcagtt cgtgatcccc     1020
acagaggcgg ttgatgagtt caagaagatc atcggcgtta ttcaagcctc gggtcactac     1080
tcgtttctca acgtgttcaa gctgttcggc ccccgcaacc aggcgccgct cagcttcccc     1140
atcccgggct ggaacatctg cgtcgacttc cccatcaagg acgggctggg gaagttcgtc     1200
agcgaactcg accgcgggt actggaattc ggcggccggc tctacaccgc caaagactcc     1260
cgtaccaccg ccgaaacctt tcatgccatg tatccgcgcg tcgacgaatg gatctccgtg     1320
cgccgcaagg tcgatccgct gcgcgtattc gcctccgaca tggcccgacg cttggagctg     1380
ctgtag                                                                 1386
```

<210> SEQ ID NO 3
<211> LENGTH: 60
<212> TYPE: PRT
<213> ORGANISM: Mycobacterium tuberculosis

<400> SEQUENCE: 3

Ser Phe Leu Asn Val Phe Lys Leu Phe Gly Pro Arg Asn Gln Ala Pro
1               5                   10                  15

Leu Ser Phe Pro Ile Pro Gly Trp Asn Ile Cys Val Asp Phe Pro Ile
            20                  25                  30

Lys Asp Gly Leu Gly Lys Phe Val Ser Glu Leu Asp Arg Arg Val Leu
        35                  40                  45

Glu Phe Gly Gly Arg Leu Tyr Thr Ala Lys Asp Ser
    50                  55                  60

<210> SEQ ID NO 4
<211> LENGTH: 60
<212> TYPE: PRT
<213> ORGANISM: Mycobacterium bovis BCG

<400> SEQUENCE: 4

Ser Phe Leu Asn Val Phe Lys Leu Phe Gly Pro Arg Asn Gln Ala Pro
1               5                   10                  15

Leu Ser Phe Pro Ile Pro Gly Trp Asn Ile Cys Val Asp Phe Pro Ile
            20                  25                  30

Lys Asp Gly Leu Gly Lys Phe Val Ser Glu Leu Asp Arg Arg Val Leu
        35                  40                  45

-continued

```
Glu Phe Gly Gly Arg Leu Tyr Thr Ala Lys Asp Ser
    50                  55                  60

<210> SEQ ID NO 5
<211> LENGTH: 60
<212> TYPE: PRT
<213> ORGANISM: Mycobacterium bovis

<400> SEQUENCE: 5

Ser Phe Leu Asn Val Phe Lys Leu Phe Gly Pro Arg Asn Gln Ala Pro
1               5                   10                  15

Leu Ser Phe Pro Ile Pro Gly Trp Asn Ile Cys Val Asp Phe Pro Ile
            20                  25

```
Gln Phe Gly Gly Arg Val Tyr Thr Ala Lys Asp Ser
    50                  55                  60
```

<210> SEQ ID NO 9
<211> LENGTH: 60
<212> TYPE: PRT
<213> ORGANISM: Mycobacterium smegmatis

<400> SEQUENCE: 9

```
Ser Phe Leu Asn Val Phe Lys Leu Phe Gly Pro Gly Asn Gln Ala Pro
1               5                   10                  15

Leu Ser Phe Pro Ile Pro Gly Trp Asn Val Cys Val Asp Phe Pro Ile
            20                  25                  30

Lys Ala Gly Leu His Glu Phe Val Thr Glu Leu Asp Arg Arg Val Leu
        35                  40                  45

Glu Phe Gly Gly Arg Leu Tyr Thr Ala Lys Asp Ser
    50                  55                  60
```

<210> SEQ ID NO 10
<211> LENGTH: 60
<212> TYPE: PRT
<213> ORGANISM: Mycobacterium aurum

<400> SEQUENCE: 10

```
Ser Phe Leu Asn Val Phe Lys Leu Phe Gly Pro Arg Asn Gln Ala Pro
1               5                   10                  15

Leu Ser Phe Pro Ile Pro Gly Trp Asn Ile Ser Val Asp Phe Pro Ile
            20                  25                  30

Lys Asp Gly Leu Gly Lys Phe Val Ser Glu Leu Asp Arg Arg Val Leu
        35                  40                  45

Glu Phe Gly Gly Arg Leu Tyr Thr Ala Lys Asp Ser
    50                  55                  60
```

<210> SEQ ID NO 11
<211> LENGTH: 60
<212> TYPE: PRT
<213> ORGANISM: Mycobacterium gilvum

<400> SEQUENCE: 11

```
Ser Phe Leu Asn Val Phe Lys Leu Phe Gly Pro Gly Asn Gln Ala Pro
1               5                   10                  15

Leu Ser Phe Pro Ile Pro Gly Trp Asn Val Cys Val Asp Phe Pro Ile
            20                  25                  30

Thr Ala Gly Leu Asn Glu Phe Leu Asn Gly Leu Asp Lys Arg Val Leu
        35                  40                  45

Gln Phe Gly Gly Arg Leu Tyr Thr Ala Lys Asp Ser
    50                  55                  60
```

<210> SEQ ID NO 12
<211> LENGTH: 60
<212> TYPE: PRT
<213> ORGANISM: Mycobacterium vanbalenii

<400> SEQUENCE: 12

```
Ser Phe Leu Asn Val Phe Lys Leu Phe Gly Pro Gly Asn Asp Ala Pro
1               5                   10                  15

Leu Ser Phe Pro Ile Pro Gly Trp Asn Val Cys Val Asp Phe Gln Ile
            20                  25                  30

Asn Pro Gly Leu Asn Glu Phe Leu Asn Gly Leu Asp Lys Arg Val Leu
```

-continued

```
                35                  40                  45

Glu Phe Gly Gly Arg Leu Tyr Thr Ala Lys Asp Ser
 50                  55                  60

<210> SEQ ID NO 13
<211> LENGTH: 60
<212> TYPE: PRT
<213> ORGANISM: Mycobacterium ulcerans

<400> SEQUENCE: 13

Ser Phe Leu Asn Val Phe Lys Leu Phe Gly Ala Gly Asn Gln Ala Pro
  1               5                  10                  15

Leu Ser Phe Pro Ile Pro Gly Trp Asn Ile Cys Val Asp Phe Pro Ile
                20                  25                  30

Lys Ala Gly Leu Asn Glu Phe Val Ser Glu Leu Asp Arg Arg Val Met
            35                  40                  45

Glu Phe Gly Gly Arg Leu Tyr Thr Ala Lys Asp Ser
 50                  55                  60

<210> SEQ ID NO 14
<211> LENGTH: 60
<212> TYPE: PRT
<213> ORGANISM: Rhodococcus spp.

<400> SEQUENCE: 14

Ser Phe Leu Asn Val Phe Lys Leu Phe Gly Glu Gly Asn Gln Ala Pro
  1               5                  10                  15

Leu Ser Phe Pro Ile Pro Gly Trp Asn Ile Cys Val Asp Phe Arg Ile
                20                  25                  30

Lys Pro Gly Leu Asn Glu Phe Val Thr Glu Leu Asp Lys Arg Val Leu
            35                  40                  45

Lys Phe Gly Gly Arg Leu Tyr Thr Ala Lys Asp Ser
 50                  55                  60

<210> SEQ ID NO 15
<211> LENGTH: 60
<212> TYPE: PRT
<213> ORGANISM: Nocardia farcinica

<400> SEQUENCE: 15

Ser Phe Leu Asn Val Phe Lys Tyr Phe Gly Gln Gly Asn Gln Ala Pro
  1               5                  10                  15

Leu Ser Phe Pro Met Pro Gly Trp Asn Val Cys Leu Asp Phe Pro Ile
                20                  25                  30

Lys Pro Gly Leu Asn Glu Phe Val Thr Glu Leu Asp Ser Arg Val Leu
            35                  40                  45

Glu Phe Gly Gly Arg Leu Tyr Thr Gly Lys Asp Ser
 50                  55                  60

<210> SEQ ID NO 16
<211> LENGTH: 60
<212> TYPE: PRT
<213> ORGANISM: Corynebacterium jeikeium

<400> SEQUENCE: 16

Ser Ala Leu Asn Val Phe Lys Leu Phe Gly Glu Gly Asn Lys Ala Pro
  1               5                  10                  15

Leu Ser Tyr Pro Met Pro Gly Trp Asn Val Cys Val Asp Leu Pro Ile
                20                  25                  30
```

```
<210> SEQ ID NO 17
<211> LENGTH: 60
<212> TYPE: PRT
<213> ORGANISM: Corynebacterium diphtheriae

<400> SEQUENCE: 17

Ser Ala Leu Asn Val Phe Lys Leu Phe Gly Glu Gly Asn Lys Ala Pro
1               5                   10                  15

Leu Ser Tyr Pro Met Pro Gly Trp Asn Val Cys Val Asp Phe Pro Ile
            20                  25                  30

Lys Pro Gly Leu Gly Ala Phe Leu Asp Asp Leu Asp Lys Arg Val Met
        35                  40                  45

Glu Phe Gly Gly Arg Leu Tyr Leu Ala Lys Glu Ser
    50                  55                  60

<210> SEQ ID NO 18
<211> LENGTH: 60
<212> TYPE: PRT
<213> ORGANISM: Corynebacterium efficiens

<400> SEQUENCE: 18

Ser Ala Leu Asn Val Phe Lys Leu Phe Gly Pro Gly Asn Arg Ala Pro
1               5                   10                  15

Leu Ser Tyr Pro Met Pro Gly Trp Asn Val Cys Val Asp Phe Pro Ile
            20                  25                  30

Arg Arg Gly Leu Gly Ala Phe Leu Asp Glu Leu Asp Glu Arg Val Met
        35                  40                  45

Glu Phe Gly Gly Arg Leu Tyr Leu Ala Lys Glu Ser
    50                  55                  60

<210> SEQ ID NO 19
<211> LENGTH: 60
<212> TYPE: PRT
<213> ORGANISM: Corynebacterium glutamicum

<400> SEQUENCE: 19

Ser Ala Leu Asn Val Phe Lys Leu Phe Gly Pro Gly Asn Arg Ala Pro
1               5                   10                  15

Leu Ser Tyr Pro Met Pro Gly Trp Asn Val Cys Val Asp Phe Pro Ile
            20                  25                  30

Arg Pro Gly Leu Gly Ala Phe Leu Asp Asp Leu Asp Lys Arg Val Met
        35                  40                  45

Glu Phe Gly Gly Arg Leu Tyr Leu Ala Lys Glu Ser
    50                  55                  60
```